United States Patent [19]
Murai et al.

[11] 4,237,132
[45] Dec. 2, 1980

[54] MORPHOLINONE DERIVATIVES AND METHOD OF USE

[75] Inventors: Hiromu Murai; Katsuya Ohata; Hiroshi Enomoto; Shoichi Chokai; Mitsuhiro Maehara; Katsuhide Saito; Takayuki Ozaki, all of Kyoto, Japan

[73] Assignee: Nippon Shinyaku Co., Ltd., Japan

[21] Appl. No.: 692,879

[22] Filed: Jun. 4, 1976

[30] Foreign Application Priority Data

Jun. 6, 1975 [JP] Japan ................................. 50-68925
Jun. 6, 1975 [JP] Japan ................................. 50-68926

[51] Int. Cl.³ ................... C07D 265/32; A61K 31/535
[52] U.S. Cl. ......................... 424/248.52; 424/248.53; 424/248.54; 424/248.55; 424/248.58; 544/158; 544/159; 544/163; 544/164; 544/172; 544/174
[58] Field of Search ................ 260/247.7 S, 247.7 W; 424/248, 248.52, 248.53, 248.54, 248.58, 248.55; 544/163, 164, 172, 174, 158, 159

[56] References Cited
U.S. PATENT DOCUMENTS
3,073,822    1/1963    Schultz et al. ............... 260/247.7 W FOREIGN PATENT DOCUMENTS
1245219    9/1971    United Kingdom ................ 260/247.7

*Primary Examiner*—Henry R. Jiles
*Assistant Examiner*—R. W. Ramsuer
*Attorney, Agent, or Firm*—Jacobs & Jacobs

[57] ABSTRACT

A series of new 4,6-disubstituted 2-morpholinone derivatives were prepared either by a reaction of corresponding epoxide derivatives with phenylglycine derivatives or by the reaction of isopropanol derivatives with carboxylic acid derivatives. The new morpholinone derivatives are useful for the prevention or the treatment of arteriosclerosis.

15 Claims, No Drawings

MORPHOLINONE DERIVATIVES AND METHOD OF USE

This invention relates to new morpholinone derivatives having the general formula:

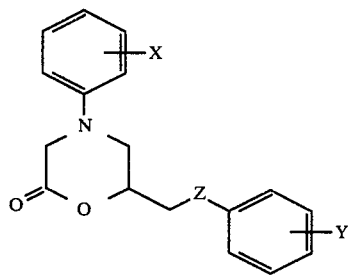

where
Z is oxygen or sulfur,
X is hydrogen, halogen, lower alkyl, lower alkoxy, carboxyl, lower alkoxycarbonyl or carbamoyl;
Y is hydrogen, halogen or lower alkyl when Z is sulfur; and
Y is hydrogen, halogen, lower alkyl, lower alkoxy, aralkoxy hydroxyl, carboxyl, lower alkoxycarbonyl or cyano when Z is oxygen;
and pharmaceutically acceptable salts thereof when X and/or Y is carboxyl or carbamoyl.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec. butyl, tert. butyl, pentyl, isopentyl, neopentyl, tert. pentyl, hexyl, and the like.

The term lower alkoxy denotes a univalent saturated branched or straight hydrocarbon chain containing from 1 to 6 carbon atoms joined to the rest of the molecule through an ether oxygen atom. Representative of such lower alkoxy groups are thus methoxy, ethoxy, propoxy, isopropoxy, butoxy, pentoxy, hexoxy, and the like.

The term lower alkoxy carbonyl denotes a univalent radical containing a lower alkoxy group joined to the rest of the molecule through a carbonyl group.

The term aralkoxy denotes a lower alkoxy group substituted by aryl of 6 to 12 carbon atoms. Representative of such aralkoxy groups are thus phenylmethoxy, phenylethoxy, phenylpropoxy, phenylbutoxy, phenylhexoxy, tolylmethoxy, tolylbutoxy, dimethylphenylmethoxy, trimethylphenylmethoxy, naphthylmethoxy, naphthylethoxy, naphthylhexoxy, and the like.

When X, Y, R and/or $R_1$ is lower alkyl, it is preferred that the lower alkyl contains from 1 to 4, most preferably 1 or 2, carbon atoms.

When X, Y, R and/or $R_1$ is lower alkoxy, it is preferred that the lower alkoxy contain from 1 to 4, most preferably 1 or 2, carbon atoms.

When X and/or Y are loweralkoxycarbonyl, it is preferred that the lower alkoxy moiety contain from 1 to 4, most preferably 1 or 2, carbon atoms.

Where Y is alkoxy, it is preferred that the alkoxy moiety contains from 1 to 4, most preferably 1 or 2, carbon atoms and that the aryl moiety is phenyl.

When X and/or Y is halogen, the halogen may be chloro, bromo, fluoro or iodo, more preferably chloro, bromo or fluoro and most preferably, chloro or bromo.

Pharmaceutically acceptable salts of compounds (I) when Y is carboxyl include metal salts, as sodium, potassium salts and the like and when Y is carbamoyl include acid addition salts, as acetate, citrate and the like.

As a result of extensive search for the compounds which have excellent triglyceride and cholesterol lowering activity in the blood and are useful for the prevention or the treatment of arteriosclerosis, the compounds (I) have been found to be very effective and this invention was achieved. The morpholinone derivatives (I) of this invention are novel compounds and possess excellent serum lipid lowering effects.

The blood lipid lowering activities are shown in Table 1.

TABLE 1

% decrease of serum lipid after the oral administration to 8 weeks-old male rats having the normal blood lipid contents at the dose of 100 mg/kg/day for 3.5 days.

| name of compound | serum cholesterol | serum triglyceride |
|---|---|---|
| 2 | 35.5 | 68.7 |
| 4 | 25.3 | 61.3 |
| 5 | 25.8 | 53.5 |
| 87 | 28.8 | 71.6 |
| Clofibrate | 42.7 | 50.7 |

Note : name of compound (arabic number) corresponds to that described in Table 2.

The values shown in Table 1 indicate the concentration changes of serum cholesterol and triglyceride after the treatment with each compound at the dose of 100 mg/kg/day for 3.5 days. These compounds were orally administered to the rat groups consisting of 10 animals by a stomach tube twice a day. Blood was usually withdrawn 4 hours after the last administration.

Serum cholesterol concentration was determined by the method of Levine and Zak, and triglyceride concentration by the method of Kessler and Lederer by means of autoanalyzer. In all examples shown in the Table 1, % decrease of the treated groups are to the non-treated reference group or control group, in which the value of control group is represented as 100%. As obvious from these results, compounds 2, 4, 5 and 87 possess more potent triglyceride lowering activities than clofibrate.

Morpholinone derivatives [I] of this invention are prepared by various methods including those known per se. Two of the most representative preparing methods are:

(1) by a condensation of the corresponding epoxide derivatives with the corresponding phenylglycine derivatives, and
(2) by a reaction of the corresponding isopropanol derivatives with the corresponding carboxylic acid derivatives.

The first method is as follows:
Namely, morpholinone derivatives having the general formula [I] are obtained by condensing epoxide derivatives of the general formula [II] with phenylglycine derivatives expressed by the general formula [III]

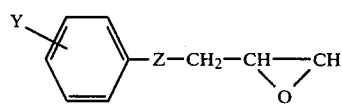

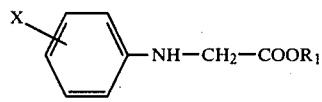

where X, Y and Z are the same as described above and $R_1$ stands for hydrogen atom or lower alkyl group.

The reactions are carried out at the temperature of 80° to 180° for 3 to 24 hours, in the absence or presence of a solvent such as benzene, toluene, xylene, N,N.-dimethylformamide, dioxane and acetic acid. These reactions are catalyzed by acids such as hydrogen chloride, sulfuric acid and acetic acid.

The second method is as follows:

Morpholinone derivatives having the general formula [I] are obtained by reacting the isopropanol derivatives expressed by the following general formula [II]' with $A.CH_2.COOR$ (where R stands for lower alkyl groups and A stands for a chlorine or bromine atom)

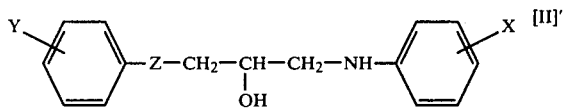

where X, Y and Z are the same as that described above.

This reaction is carried out in a protic solvent such as alcohols, N.N-dimethylformamide and dimethylsulfoxide. In this case, it is advantageous to use inorganic bases such as potassium carbonate and sodium bicarbonate for the removal of the acid formed. The reaction is preferably carried out at a temperature range of 80° to 180° C.

Isopropanol derivatives having the general formula [II]' which are the starting materials are obtained from the reaction between the epoxide derivative and aniline derivative of the following general formulas [III]' and [IV], respectively. Starting materials are obtained from epoxide derivatives and aniline derivatives expressed by the following general formulas [III]' and [IV], respectively.

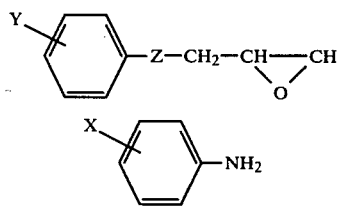

X, Y and Z are the same as defined above. The reaction may be carried out in an organic solvent, such as ethanol, under reflux.

The following examples are to illustrate some representative embodiments of the above two methods. It is, however, to be understood that this invention is never limited thereto.

In the following examples, the Example I relates to the method (1) and the Example II relates to the method (2).

EXAMPLE I

The preparative method for 4-(m-chlorophenyl)-6-(p-chlorophenoxymethyl)-2-morpholinone 5.3 g (0.025 moles) of N-(m-chlorophenyl) glycine ethylester and 4.6 g (0.025 moles) of p-chlorophenylglycidyl ether were heated at 180° for 24 hours. Crystallization of the cooled reactant from ethanol gave 5.0 g of a solid. The filtrate was concentrated in vacuo and the resulting residue was refluxed in 10 ml of acetic acid for 6 hr. After evaporation of acetic acid under reduced pressure, crystallization of the residue from ethanol gave further 1.5 g of the solid. Five g (57%) of the crystal was obtained by recrystallization of the combined products from ethanol and benzene m.p.128°–129°.

| elemental analysis : $C_{17}H_{15}ClNO_3$ | | | | |
|---|---|---|---|---|
| | C | H | N | Cl |
| calcd | 57.45 | 4.29 | 3.97 | 20.13 |
| found | 57.34 | 4.19 | 3.95 | 20.07 |

A series of the compounds [I] were prepared by the same procedure. They are described in Table II. The compound shown in example I corresponds to compound 28.

EXAMPLE II

The preparative method for 6-(p-chlorophenoxymethyl)-4-phenyl-2-morpholinone (1) The preparation of 1-anilino-3-(p-chlorophenoxy)-2-propanol After 44 g (0.238 moles) of p-chlorophenylglycidyl ether and 66 g (0.71 moles) of aniline were dissolved in 200 ml of ethanol and the resulting solution was refluxed for 3 hr, ethanol was evaporated under reduced pressure. The resulting residue was solidified with ethanol and n-hexane. The solid was collected by filtration and washed with n-hexane. Recrystallization of this product from ethanol without drying gave 34.6 g of crystals (52.3%) with a melting point of 83° to 84.5°.

| elemental analysis : $C_{15}H_{16}ClNO_2$ | | | | |
|---|---|---|---|---|
| | C | H | N | Cl |
| calcd | 64.86 | 5.80 | 5.04 | 12.76 |
| found | 65.08 | 5.83 | 4.95 | 12.67 |

(2) The preparation of 6-(p-chlorophenoxymethyl)-4-phenyl-2-morpholinone

Two grams (0.0072 moles) of 1-anilino-3-(p-chlorophenoxy)-2-propanol [prepared in part (1)], 1.2 g (0.0087 moles) of $K_2CO_3$ and 2.9 g (0.0174 moles) of ethyl bromoacetate were added to 20 ml of N,N-dimethylformamide. The resulting mixture was refluxed for 5 hr with stirring. Concentration of the reaction mixture and addition of ethyl acetate and water to the residue gave a solid. The solid was collected by filtration and washed with ethyl acetate and water and dried (0.5 g). The filtrate was acidified with 10% aqueous hydrochloric acid and the organic layer was washed with water and dried over anhydrous magnesium sulfate. After the evaporation of ethyl acetate, 20 ml of acetic acid was added to the residue and refluxed for 3 hr. The reaction mixture was concentrated under reduced pressure, and 1.3 g of the solid was obtained by crystallizing the residue from ether. Recrystallization of the combined solids (1.8 g) from benzene gave 1.3 g (57%) of crystals, m.p.142°-144°.

| elemental analysis : $C_{17}H_{16}ClNO_3$ | | | | |
|---|---|---|---|---|
|  | C | H | N | Cl |
| calcd | 64.25 | 5.08 | 4.41 | 11.16 |
| found | 65.15 | 4.88 | 4.52 | 11.21 |

A series of the compounds [I] were prepared by the same procedure. They are described in Table II. Compound shown in Example II corresponds to the compound number-2.

TABLE 2

| Compound number | X | Y | Formula | M.W. | Mp. (°C.) |
|---|---|---|---|---|---|
|  | Z = O |  |  |  |  |
| 1 | H | H | $C_{17}H_{17}NO_3$ | 283.31 | 108.5–111 |
| 2 | H | p-Cl | $C_{17}H_{16}ClNO_3$ | 317.77 | 142–144 |
| 3 | H | o-Cl | $C_{17}H_{16}ClNO_3$ | 317.77 | 107–108 |
| 4 | H | p-Br | $C_{17}H_{16}BrNO_3$ | 362.22 | 137–138 |
| 5 | H | p-F | $C_{17}H_{16}FNO_3$ | 301.33 | 111–112.5 |
| 6 | H | p-CH$_3$ | $C_{18}H_{19}NO_3$ | 297.34 | 138.5–140.5 |
| 7 | H | o-CH$_3$ | $C_{18}H_{19}NO_3$ | 297.34 | 87–89 |
| 8 | H | p-t-Bu | $C_{21}H_{25}NO_3$ | 339.42 | 106–107.5 |
| 9 | H | p-OCH$_3$ | $C_{18}H_{19}NO_4$ | 313.34 | 104–105 |
| 10 | H | o-OC$_2$H$_5$ | $C_{19}H_{21}NO_4$ | 327.37 | 119–120 |
| 11 | H | p-OCH$_2$—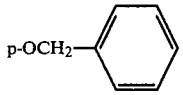 | $C_{24}H_{23}NO_4$ | 389.43 | 126–129 |
| 12 | H | p-COOCH$_3$ | $C_{19}H_{19}NO_4$ | 341.35 | 118–119 |
| 13 | H | p-COOC$_2$H$_5$ | $C_{20}H_{21}NO_5$ | 355.38 | 96–97 |
| 14 | p-Cl | H | $C_{17}H_{16}ClNO_3$ | 317.77 | 89–91 |
| 15 | p-Cl | p-Cl | $C_{17}H_{15}Cl_2NO_3$ | 352.21 | 118–119 |
| 16 | p-Cl | o-Cl | $C_{17}H_{15}Cl_2NO_3$ | 352.21 | 107–109 |
| 17 | p-Cl | p-CH$_3$ | $C_{18}H_{18}ClNO_3$ | 331.79 | 134–135 |
| 18 | p-Cl | m-CH$_3$ | $C_{18}H_{18}ClNO_3$ | 331.79 | 75–77 |
| 19 | p-Cl | o-CH$_3$ | $C_{18}H_{18}ClNO_3$ | 331.79 | 77.5–80 |
| 20 | p-Cl | p-t-Bu | $C_{21}H_{24}ClNO_3$ | 373.88 | 120–121.5 |
| 21 | p-Cl | p-C$_2$H$_5$ | $C_{19}H_{20}ClNO_3$ | 345.82 | 91–93 |
| 22 | p-Cl | p-OCH$_2$—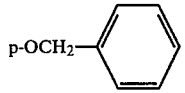 | $C_{24}H_{22}ClNO_4$ | 423.88 | 119–121 |
| 23 | p-Cl | p-COOCH$_3$ | $C_{19}H_{18}ClNO_5$ | 375.80 | 125–128.5 |
| 24 | p-Cl | p-COOC$_2$H$_5$ | $C_{20}H_{20}ClNO_5$ | 389.83 | 155–157 |
| 25 | p-CH$_3$ | p-Cl | $C_{18}H_{18}ClNO_3$ | 331.79 | 129.5–131 |
| 26 | p-C$_2$H$_5$ | p-Cl | $C_{19}H_{20}ClNO_3$ | 345.82 | 129–131 |
| 27 | m-Cl | H | $C_{17}H_{16}ClNO_3$ | 317.76 | 107–108 |
| 28 | m-Cl | o-Cl | $C_{17}H_{15}ClNO_3$ | 352.21 | 128–129 |
| 29 | m-Cl | o-Cl | $C_{17}H_{15}ClNO_3$ | 352.21 | 120.5–121.5 |
| 30 | m-Cl | p-CH$_3$ | $C_{18}H_{18}ClNO_3$ | 331.80 | 103–104 |
| 31 | m-Cl | m-CH$_3$ | $C_{18}H_{18}ClNO_3$ | 331.80 | 83.5–85 |
| 32 | m-Cl | o-CH$_3$ | $C_{18}H_{18}ClNO_3$ | 331.80 | 103–104 |
| 33 | m-Cl | p-OCH$_3$ | $C_{18}H_{18}ClNO_4$ | 347.80 | 89–90.5 |
| 34 | m-Cl | p-OCH$_2$—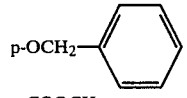 | $C_{24}H_{22}ClNO_4$ | 423.38 | 137.5–140 |
| 35 | m-Cl | p-COOCH$_3$ | $C_{19}H_{18}ClNO_5$ | 375.81 | 124.5–126 |
| 36 | m-Cl | p-COOC$_2$H$_5$ | $C_{20}H_{20}ClNO_5$ | 389.94 | 117–118.5 |
| 37 | m-Cl | p-COOH | $C_{18}H_{16}ClNO_5$ | 361.78 | 217–219.5 |
| 38 | m-Cl | p-CN | $C_{18}H_{15}ClN_2O_3$ | 342.78 | 167.5–169 |
| 39 | m-OCH$_3$ | H | $C_{18}H_{19}NO_4$ | 313.34 | 97.5–101 |
| 40 | m-OCH$_3$ | p-Cl | $C_{18}H_{18}ClNO_4$ | 347.79 | 111–111.5 |
| 41 | m-OCH$_3$ | o-Cl | $C_{18}H_{18}ClNO_4$ | 347.79 | 104–105 |
| 42 | m-OCH$_3$ | p-CH$_3$ | $C_{19}H_{21}NO_4$ | 327.37 | 100–101 |
| 43 | m-OCH$_3$ | m-CH$_3$ | $C_{19}H_{21}NO_4$ | 327.37 | 103.5–104 |
| 44 | m-OCH$_3$ | o-CH$_3$ | $C_{19}H_{21}NO_4$ | 327.37 | 94.5–95.5 |
| 45 | m-OCH$_3$ | p-OCH$_3$ | $C_{19}H_{21}NO_5$ | 343.37 | 109–110 |
| 46 | m-OCH$_3$ | p-OCH$_2$—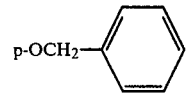 | $C_{25}H_{25}NO_5$ | 419.46 | 136.5–137.5 |
| 47 | m-OCH$_3$ | p-OH | $C_{18}H_{19}NO_5$ | 329.34 | 138.5–139.5 |
| 48 | m-OCH$_3$ | p-COOCH$_3$ | $C_{20}H_{21}NO_6$ | 371.38 | 134–135 |
| 49 | m-OCH$_3$ | p-COOC$_2$H$_5$ | $C_{21}H_{23}NO_6$ | 385.40 | 122–123 |

TABLE 2-continued

| Compound number | X | Y | Formula | M.W. | Mp. (°C.) |
|---|---|---|---|---|---|
| 50 | m-OCH$_3$ | p-COOH | C$_{19}$H$_{19}$NO$_6$ | 357.35 | 207–209 |
| 51 | m-OCH$_3$ | p-CN | C$_{19}$H$_{18}$N$_2$O$_4$ | 338.35 | 133.5–135 |
| 52 | p-COOCH$_3$ | H | C$_{19}$H$_{19}$NO$_5$ | 341.35 | 140.5–142 |
| 53 | p-COOCH$_3$ | p-Cl | C$_{19}$H$_{18}$ClNO$_5$ | 375.81 | 129–131 |
| 54 | p-COOCH$_3$ | o-Cl | C$_{19}$H$_{18}$ClNO$_5$ | 375.81 | 137–139 |
| 55 | p-COOCH$_3$ | p-CH$_3$ | C$_{20}$H$_{21}$NO$_5$ | 355.35 | 150–151 |
| 56 | p-COOCH$_3$ | m-CH$_3$ | C$_{20}$H$_{21}$NO$_5$ | 355.38 | 123.5–125 |
| 57 | p-COOCH$_3$ | o-CH$_3$ | C$_{20}$H$_{21}$NO$_5$ | 355.38 | 126–128 |
| 58 | p-COOCH$_3$ | p-OCH$_3$ | C$_{20}$H$_{21}$NO$_6$ | 371.38 | 126–127.5 |
| 59 | p-COOCH$_3$ | p-COOCH$_3$ | C$_{21}$H$_{21}$NO$_7$ | 399.39 | 142.5–146 |
| 60 | p-COOCH$_3$ | p-COOC$_2$H$_5$ | C$_{22}$H$_{23}$NO$_7$ | 413.41 | 180–181.5 |
| 61 | p-COOCH$_3$ | p-CN | C$_{20}$H$_{18}$N$_2$O$_5$ | 366.36 | 198–200.5 |
| 62 | p-COOC$_2$H$_5$ | H | C$_{20}$H$_{21}$NO$_5$ | 335.38 | 106–108 |
| 63 | p-COOC$_2$H$_5$ | p-Cl | C$_{20}$H$_{20}$ClNO$_5$ | 389.83 | 136.5–138.5 |
| 64 | p-COOC$_2$H$_5$ | o-Cl | C$_{20}$H$_{20}$ClNO$_5$ | 389.83 | 143.5–145 |
| 65 | p-COOC$_2$H$_5$ | p-CH$_3$ | C$_{21}$H$_{23}$NO$_5$ | 369.40 | 139.5–140 |
| 66 | p-COOC$_2$H$_5$ | m-CH$_3$ | C$_{21}$H$_{23}$NO$_5$ | 369.40 | 113–114 |
| 67 | p-COOC$_2$H$_5$ | o-CH$_3$ | C$_{21}$H$_{23}$NO$_5$ | 369.40 | 104–105 |
| 68 | p-COOC$_2$H$_5$ | p-OCH$_3$ | C$_{21}$H$_{23}$NO$_6$ | 385.40 | 132.5–134 |
| 69 | p-COOC$_2$H$_5$ | p-OCH$_2$–C$_6$H$_5$ | C$_{27}$H$_{27}$NO$_6$ | 461.49 | 141–143 |
| 70 | p-COOC$_2$H$_5$ | p-COOCH$_3$ | C$_{22}$H$_{23}$NO$_7$ | 413.41 | 156–158 |
| 71 | p-COOC$_2$H$_5$ | p-COOC$_2$H$_5$ | C$_{23}$H$_{25}$NO$_7$ | 427.44 | 157–158.5 |
| 72 | p-COOH | H | C$_{18}$H$_{17}$NO$_5$ | 327.32 | 234–236 |
| 73 | p-COOH | p-Cl | C$_{18}$H$_{16}$NO$_5$ | 361.78 | 236–238 |
| 74 | p-COOH | o-Cl | C$_{18}$H$_{16}$ClNO$_5$ | 361.78 | 225–226.5 |
| 75 | p-COOH | p-OCH$_3$ | C$_{19}$H$_{19}$NO$_6$ | 357.35 | 219.5–221 |
| 76 | p-CONH$_2$ | H | C$_{18}$H$_{18}$N$_2$O$_4$ | 326.24 | 200–201 |
| 77 | p-CONH$_2$ | p-Cl | C$_{18}$H$_{17}$ClN$_2$O$_4$ | 360.79 | 191–192 |
| 78 | p-CONH$_2$ | o-Cl | C$_{18}$H$_{17}$ClN$_2$O$_4$ | 360.79 | 185–187 |
| 79 | p-CONH$_2$ | p-CH$_3$ | C$_{19}$H$_{20}$N$_2$O$_4$ | 340.37 | 201–202.5 |
| 80 | p-CONH$_2$ | m-CH$_3$ | C$_{19}$H$_{20}$N$_2$O$_4$ | 340.37 | 176–177.5 |
| 81 | p-CONH$_2$ | p-OCH$_3$ | C$_{19}$H$_{20}$N$_2$O$_5$ | 356.37 | 191–193 |
| 82 | p-CONH$_2$ | p-COOCH$_3$ | C$_{20}$H$_{20}$N$_2$O$_6$ | 384.38 | 251–253 |
| 83 | p-CONH$_2$ | p-COOC$_2$H$_5$ | C$_{21}$H$_{22}$N$_2$O$_6$ | 398.40 | 204–205.5 |
| 84 | p-CONH$_2$ | p-OCH$_2$–C$_6$H$_5$ | C$_{25}$H$_{24}$N$_2$O$_5$ | 432.46 | 211–212 |
| 85 | p-CONH$_2$ | p-CN | C$_{19}$H$_{17}$N$_3$O$_4$ | 351.35 | 235–237 |
| 86 | p-CONH$_2$ | o-CH$_3$ | C$_{19}$H$_{20}$N$_2$O$_4$ | 340.37 | 170–171 |
| Z = S | | | | | |
| 87 | H | p-Cl | C$_{17}$H$_{16}$ClNO$_2$S | 333.84 | 111–113 |
| 88 | p-CH$_3$ | p-CH$_3$ | C$_{19}$H$_{21}$NO$_2$S | 327.42 | 92–93.5 |
| 89 | p-CH$_3$ | p-Cl | C$_{18}$H$_{18}$ClNO$_2$S | 312.40 | 110–111 |
| 90 | p-C$_2$H$_5$ | p-Cl | C$_{19}$H$_{20}$ClNO$_2$S | 361.89 | 89–90.5 |
| 91 | m-Cl | H | C$_{17}$H$_{16}$ClNO$_2$S | 333.85 | 91–92 |
| 92 | m-Cl | p-Cl | C$_{17}$H$_{15}$Cl$_2$NO$_2$S | 368.30 | 108–109.5 |
| 93 | m-OCH$_3$ | H | C$_{18}$H$_{19}$NO$_3$S | 329.42 | 66–67.5 |
| 94 | m-OCH$_3$ | p-Cl | C$_{18}$H$_{18}$ClNO$_3$S | 368.87 | 105–106 |
| 95 | p-COOCH$_3$ | H | C$_{19}$H$_{19}$NO$_4$S | 357.43 | 135.5–138 |
| 96 | p-COOCH$_3$ | p-Cl | C$_{19}$H$_{18}$ClNO$_4$S | 391.87 | 135–136 |
| 97 | p-COOC$_2$H$_5$ | p-Cl | C$_{20}$H$_{20}$ClNO$_4$S | 405.90 | 147–149 |

The compounds (I) of the invention may be used as such or in combination with a pharmaceutically acceptable solid or liquid inert diluent or carrier in the same dosage and in the same routes of administration as conventional agents for reducing serum cholesterol and triglycerides and for prevention of arteriosclerosis. The daily dosage will be determined by the physician for the particular patient, but generally a daily dosage of from about 50 mg to about 5 grams will be satisfactory, preferably about 100 mg to about 2 grams.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

When X or Y is carboxyl, the present invention also pertains to the physiologically acceptable salts of the foregoing compounds with alkali metals, alkaline earth metals, ammonia and organic amines as, for example, the sodium salt, the potassium salt, the calcium salt, and the salts with amines such as ethylamine, triethylamine, ethanolamine, diethylaminoethanol, ethylenediamine, piperidine, morpholine, 2-piperidinoethanol, benzylamine, procaine and the like.

As indicated, the present invention also pertains to the physiologically acceptable non-toxic acid addition salts when X or Y is carbamoyl. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

What is claimed is:

1. A compound selected from the group consisting of a morpholinone of the formula:

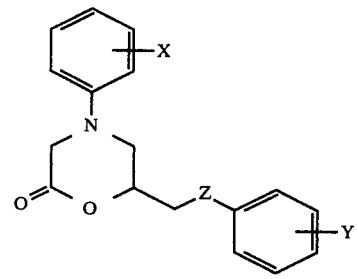

wherein
  Z is oxygen or sulfur;
  X is hydrogen, halogen, lower alkyl, lower alkoxy, carboxyl, or carbo(lower alkoxy) or carbamoyl;
  Y is hydrogen, halogen or lower alkyl when Z is sulfur; and
  Y is hydrogen, halogen, lower alkyl, lower alkoxy, benzyloxy, hydroxy, carboxy, carbo(lower alkoxy) or cyano when Z is oxygen;
and the pharmaceutically acceptable salts thereof when X or Y is carboxyl or X is carbamoyl.

2. A compound selected from the group consisting of a morpholinone of the formula:

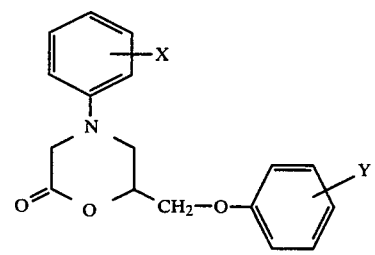

wherein
  X is hydrogen, halogeno, lower alkyl, lower alkoxy, carboxy or carbo(lower alkoxy), and
  Y is hydrogen, halogeno, lower alkoxy or carbo(lower alkoxy), and
the pharmaceutically acceptable salts of said morpholinones in which X is carboxy.

3. A compound according to claim 2 wherein X is hydrogen, halogeno, lower alkyl or lower alkoxy and Y is hydrogen, halogeno or lower alkyl.

4. A compound according to claim 2 wherein X is hydrogen, chloro, methyl, ethyl, methoxy, carboxy, carbomethoxy, carbethoxy and Y is hydrogen, chloro, bromo, fluoro, methoxy, ethoxy, carbomethoxy or carbethoxy.

5. A compound according to claim 4 wherein Y is in the para position.

6. A compound selected from the group consisting of a morpholinone of the formula:

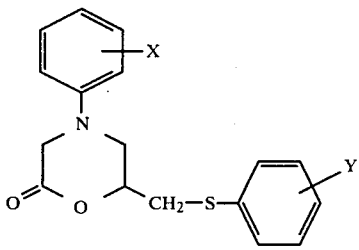

wherein
X is hydrogen, halogeno, lower alkyl, lower alkoxy, carboxy or carbo(lower alkoxy), and
Y is hydrogen or halogeno, and
the pharmaceutically acceptable salts of said morpholinones in which X is carboxy.

7. A compound according to claim 6 wherein X is hydrogen, halogeno, lower alkyl or lower alkoxy and Y is hydrogen or halogeno.

8. A compound according to claim 6 wherein X is hydrogen, chloro, methyl, ethyl, methoxy, carboxy, carbomethoxy or carbethoxy and Y is hydrogen or chloro.

9. A compound according to claim 8 wherein Y is in the para position.

10. The compound according to claim 2, wherein and X and Y are hydrogen.

11. The compound according to claim 2, wherein X is hydrogen and Y is chloro in the para-position.

12. The compound according to claim 2, wherein X is hydrogen and Y is fluoro in the para-position.

13. The compound according to claim 6, wherein X is hydrogen and Y is chloro in the para-position.

14. A pharmaceutical composition for reducing serum cholesterol and triglycerides, which comprises an amount of the compound of claim 1 effective to reduce serum cholesterol and triglycerides in combination with a pharmaceutically acceptable solid or liquid inert diluent or carrier therefor.

15. A method of reducing serum cholesterol and triglycerides, which comprises administering to an animal or human in need thereof an amount of a compound selected from the group consisting of a morpholinone of the formula:

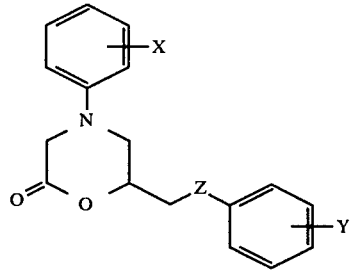

wherein
Z is oxygen or sulfur;
X is hydrogen, halogen, lower alkyl, lower alkoxy, carboxyl, or carbo(lower alkoxy) or carbamoyl;
Y is hydrogen, halogen or lower alkyl when Z is sulfur; and
Y is hydrogen, halogen, lower alkyl, lower alkoxy, benzyloxy, hydroxy, carboxy, carbo(lower alkoxy) or cyano when Z is oxygen;
and the pharmaceutically acceptable salts thereof when X or Y is carboxyl or X is carbamoyl effective to reduce serum cholesterol and triglycerides.

* * * * *